United States Patent [19]

Tokura et al.

[11] Patent Number: 5,267,217
[45] Date of Patent: Nov. 30, 1993

[54] APPARATUS FOR AND METHOD OF DETECTING SHAPE OF SOLDER PORTION

[75] Inventors: Nobufumi Tokura; Shoichi Nishi, both of Fukuoka, Japan

[73] Assignee: Matsushita Electric Industrial Co., Ltd., Osaka, Japan

[21] Appl. No.: 671,413

[22] Filed: Mar. 20, 1991

[30] Foreign Application Priority Data

Mar. 20, 1990 [JP] Japan ............................ 2-70413

[51] Int. Cl.⁵ .......................................... G01N 21/00
[52] U.S. Cl. ................................................... 356/237
[58] Field of Search .............. 356/237, 394; 382/8, 382/48

[56] References Cited

U.S. PATENT DOCUMENTS

| | | | |
|---|---|---|---|
| 4,688,939 | 8/1987 | Ray | 356/237 |
| 4,759,072 | 7/1988 | Yamane et al. | 356/237 |
| 5,032,735 | 7/1991 | Kobayashi et al. | 350/572 |

FOREIGN PATENT DOCUMENTS 0175606 8/1987 Japan ............................ 356/373

*Primary Examiner*—Richard A. Rosenberger
*Assistant Examiner*—K. P. Hantis
*Attorney, Agent, or Firm*—Lowe, Price, LeBlanc & Becker

[57] ABSTRACT

The surface of a solder portion is specular. Besides, it includes a flat plane, a steep inclined plane and a gentle inclined plane. Accordingly, when light is projected toward the solder portion in a specified direction and light reflected from the solder portion is observed with a camera, an image having the contrast between brightness and darkness is obtained. The present invention utilizes such light reflection characteristics of the solder portion in order to judge whether the shape of the solder portion is good or bad. According to the present invention, light is projected toward a solder portion for bonding the electrode of an electrical component to a substrate, in directions of at least two angles, and the solder portion is observed by a camera disposed above this solder portion. Subsequently, image data items picked up at the respective angles by the camera are stored in corresponding image memories, and the image data items are processed in combination by an image processor. Subsequently, image data having the feature of the shape of the solder portion as generated by the processing is stored in an image memory, and the quality of the shape of the solder portion is judged on the basis of the generated image data by a CPU.

4 Claims, 5 Drawing Sheets

FIG. 2(a)
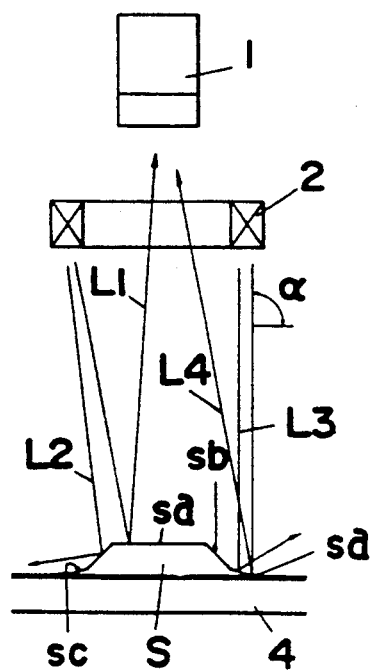
FIG. 3(a)
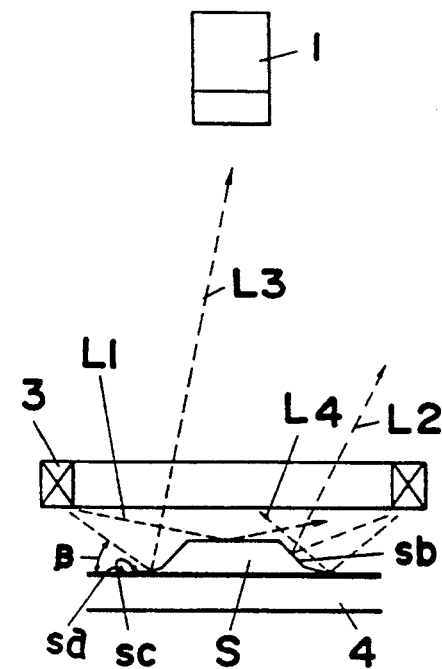
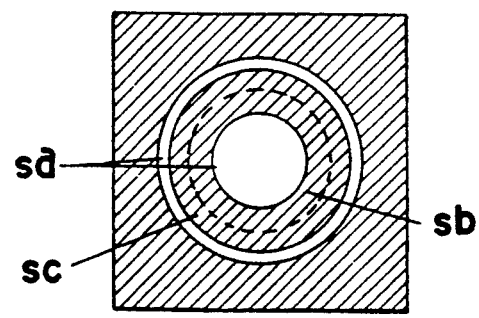
FIG. 2(b)
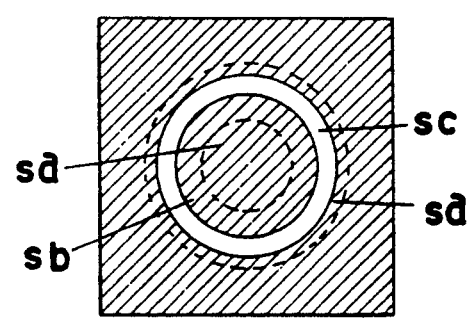
FIG. 3(b)

FIG. 4

| | O.K. | N.G. | N.G. |
|---|---|---|---|
| | | | |
| M1 MULTIVALUED DATA (FIRST LIGHT SOURCE) | a1 | b1 | c1 |
| M2 MULTIVALUED DATA (SECOND LIGHT SOURCE) | a2 | b2 | c2 |
| M1b BINARY DATA | a3 | b3 | c3 |
| M2a MULTIVALUED DATA | a4 | b4 | c4 |
| M3 BINARY DATA | a5 | b5 | c5 |
| CRITERIA | Pa BLACK RING ⇨ GOOD | Pb DOUBLE BLACK RING ⇨ OVERMUCH SOLDER | Pc SMALL BLACK RING ⇨ DEFICIENT SOLDER |

FIG. 6

| | M1 MULTIVALUED DATA | M2 MULTIVALUED DATA | M1b BINARY DATA | M2a MULTIVALUED DATA | M3 BINARY DATA | CRITERIA |
|---|---|---|---|---|---|---|
| O.K. | A1 | A2 | A3 | A4 | A5 | PA BLACK HAVING AN AREA WITHIN CERTAIN LIMITS AND NOT CONTAINING WHITE IN EXCESS OF A PREDETERMINED AREA ⇔ GOOD |
| N.G. | B1 | B2 | B3 | B4 | B5 | PB DOUBLE BLACK RING ⇔ OVERMUCH SOLDER |
| N.G. | C1 | C2 | C3 | C4 | C5 | PC SMALL AREA OF BLACK PART ⇔ DEFICIENT SOLDER |
| N.G. | D1 | D2 | D3 | D4 | D5 | PD PSEUDO-DOUBLE BLACK RING ⇔ LEAD AFLOAT |

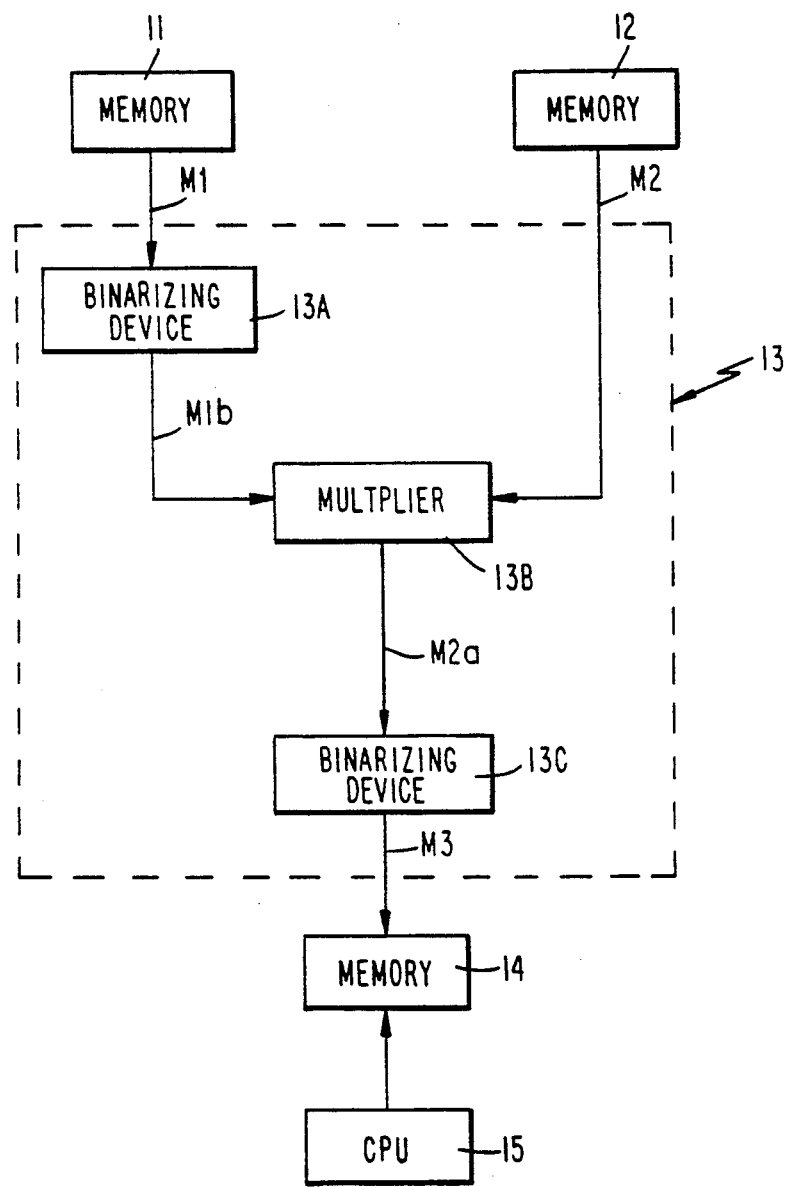

APPARATUS FOR AND METHOD OF DETECTING SHAPE OF SOLDER PORTION

BACKGROUND OF THE INVENTION:

1. Field of the Invention

The present invention relates to an apparatus for and a method of detecting the shape of a solder portion. More particularly, it consists in a technique in which image data items obtained at different projection angles of light are combined, thereby to acquire image data having the features of the shape of a solder portion, and whether the shape of the solder portion is good or bad is judged on the basis of the acquired image data.

2. Description of the Prior Art

The shape of a solder portion for bonding the electrode of an electrical component to a substrate is generally detected by projecting light toward the solder portion and observing this solder portion with a camera. More specifically, the surface of the solder portion is a specular oblique surface. Accordingly, when the light is projected from above the solder portion and this solder portion is observed with the camera from above it, the light is reflected sidewards, and reflected light hardly enters the camera, so that the solder portion is observed dark. In the prior art, therefore, a detection area surrounding the solder portion is set, the number of pixels in black existing within the area is compared with a preset number by a computer, and whether the shape of the solder portion is good or bad is judged in accordance with the compared result.

Since, however, the prior-art method judges the quality of the shape of the solder portion on the basis of only the black information picked up by the camera, it is liable to misjudge due to the small amount of information on which the judgement is founded. As a concrete example, in a case where the camera has erroneously observed the surface of a resist sideward of the target solder portion without observing this solder portion, the method misjudges that the solder is sufficiently existent, because the resist surface is observed dark. Likewise, in a case where a light source is not lit up or where the substrate to be tested does not lie at a test position, the method has the problem of erroneously judging the sufficient existence of the solder, because a black image is picked up by the camera.

SUMMARY OF THE INVENTION

The present invention therefore has for its object to provide a technique for detecting the shape of a solder portion in which image information forming the foundation of the judgement of the quality of the solder shape is more increased in number, whereby the quality can be judged more accurately.

In order to accomplish the object, the present invention constructs an apparatus for detecting the shape of a solder portion, out of a camera by which the solder portion for bonding an electrode of an electrical component to a substrate is observed from above, light source means for projecting light toward the solder portion in directions of at least two angles, a first image memory which is connected to said camera and which stores therein image data picked up by said camera when the light is projected at one of the angles, a second image memory which is connected to said camera and which stores therein image data picked up by said camera when the light is projected at the other angle, an image processor which is connected to said first and second image memories and which combines the image data items stored in the two image memories, thereby to generate image data having a feature of the shape of the solder portion, a third image memory which is connected to said image processor and which stores therein the generated image data, and a CPU which is connected to said third image memory and which judges a quality of the shape of the solder portion from the image data stored in said third image memory.

According to the above construction, there are obtained the image data items in the cases of projecting the light toward the solder portion at the plurality of angles. Then, the image data manifesting the features of the solder shape favorably is acquired by combining the image data items, and whether the shape of the solder portion is good or bad is judged on the basis of the acquired image data.

BRIEF DESCRIPTION OF THE DRAWINGS

FIGS. 2(a) and 3(a) and FIGS. 2(b) and 3(b) are side views and image data patterns, respectively, for elucidating the principle of the present invention as to the detection of the shape of a solder model;

FIG. 4 is a diagram showing image data items in the example of FIG. 1;

FIG. 6 is a diagram showing image data items in the example of FIG. 5.

FIG. 7 is a diagram showing a part of another embodiment of this invention.

PREFERRED EMBODIMENTS OF THE INVENTION

Now, embodiments of the present invention will be described with reference to the drawings.

EXAMPLE 1

Figure 1:
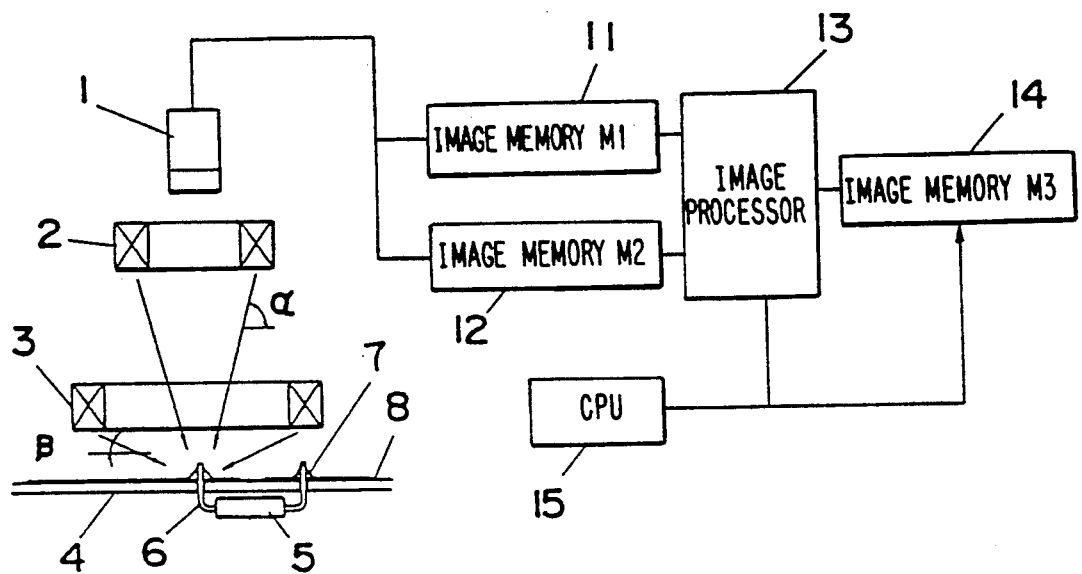
FIG. 1 is a diagram of the whole arrangement of a shape detecting apparatus in an example of the present invention.

FIG. 1 shows a shape detecting apparatus, which includes a camera 1, a first light source 2 and a second light source 3. Numeral 4 designates a substrate, on which an electrical component 5 is mounted. Numeral 6 designates the electrode of the electrical component 5, which is inserted in the substrate 4 and is bonded thereto by a solder portion 7. Shown at numeral 8 is a resist with which the substrate 4 is coated.

The first light source 2 projects light at a wide angle $\alpha$ defined with respect to the plane of the substrate 4 (at a steep gradient relative to the substrate plane). On the other hand, the second light source 3 projects light at a narrow angle $\beta$ defined with respect to the substrate plane (at a gentle gradient relative to the substrate plane). The camera 1 is disposed above the solder portion 7, and it picks up the images of the solder portion 7 with the light projection angles changed-over by selectively lighting up the first light source 2 and the second light source 3.

The first light source 2 projects the light on the entire surface of the solder portion 7 at the widest possible angle to this solder portion, desirably perpendicularly thereto. For this purpose, a ring-shaped light source or a planar one is used as the first light source 2. Meanwhile, the second light source 3 projects the light uniformly on the entire surface of the solder portion 7 sideward of this solder portion. For this purpose, a ring-shaped light source is used as the second light source 3. By the way, the light sources 2 and 3 may well be replaced with a system in which only one light source is disposed and in which the light projection angles for the solder portion are changed-over by vertically moving the single light source.

The camera 1 is connected to a first image memory 11 and a second image memory 12. The first image memory 11 stores therein image data M1 picked up in the case of projecting the light on the solder portion 7 from the first light source 2. On the other hand, the second image memory 12 stores therein image data M2 picked up in the case of projecting the light on the solder portion 7 from the second light source 3.

Numeral 13 indicates an image processor, which combines the image data M1 and the image data M2 so as to generate image data M3 and which stores the generated data M3 in a third image memory 14. Shown at numeral 15 is a CPU, which judges the quality of the shape of the solder portion 7 on the basis of the image data M3 of the image memory 14 as will be described in detail later.

The light reflection characteristics of solder will be explained before the description of an image processing method according to the present invention.

FIGS. 2(a) and 2(b) and FIGS. 3(a) and 3(b) show situations in which a solder model S is being observed by the optical system stated above, and images which have been picked up by the camera 1. The solder model S has flat planes sa, a steep inclined plane sb and a gentle inclined plane sc. As illustrated in FIG. 2(a), in the case where the light is projected on the solder model S at the wide angle $\alpha$ from the light source 2, the top flat plane sa reflects the light toward the camera 1 and is therefore observed to be white or bright (refer to an arrow L1). In addition, the steep inclined plane sb and the gentle inclined plane sc succeeding thereto reflect the light sidewards, and the beams of light reflected from them do not enter the camera 1, so that they are observed to be black or dark (refer to respective arrows L2 and L3). Besides, the substantially flat plane sa which lands on the substrate 4 reflects the projected light toward the camera 1 and is therefore observed to be bright (refer to an arrow L4). As a whole, accordingly, the solder models is observed in terms of the contrast between black and white as depicted in FIG. 2(b).

Meanwhile, as illustrated in FIG. 3(a), in the case where the light is projected on the solder model S at the narrow angle $\beta$ from the light source 3, the whole solder model S is observed in terms of the contrast between black and white as depicted in FIG. 3(b), owing to reflection characteristics similar to the foregoing. In this case, only the gentle inclined plane sc reflects the light toward the camera 1 and is observed to be bright, whereas the other planes sa and sb are observed to be dark. Arrows L1, L2, L3 and L4 in FIG. 3(a) indicate the beams of reflected light from the upper flat plane sa, the steep inclined plane sb, the gentle inclined plane sc and the lower flat plane sa, respectively. Incidentally, a solder portion applied on a substrate is usually in possession of the three sorts of continuous planes of the steep inclined plane sb, the gentle inclined plane sc and the flat planes sa as demonstrated by the solder model S.

The present invention judges whether the solder shape is good or bad, by utilizing such light reflection characteristics of the solder. Next, there will be described the image processing method in the case where actual solder portions are observed by the shape detecting apparatus stated before.

FIG. 4 shows the sectional shapes of the solder portions 7 as depicted in FIG. 1, and the image data items thereof. Referring to FIG. 4, symbols 7a, 7b and 7c in the uppermost column indicate the sectional shapes of the solder portions which are good, no-good due to overmuch solder and no-good due to deficient solder, respectively. Besides, symbols sa, sb and sc denote a flat plane, a steep inclined plane and a gentle inclined plane, respectively. Shown at numeral 10 is a circuit pattern.

Multivalued image data M1 is picked up by the camera 1 when the first light source 2 is lit up. On the other hand, multivalued image data M2 is picked up by the camera 1 when the second light source 3 is lit up. It is obvious from the light reflection characteristics of the solder model S illustrated in FIGS. 2(a) thru 3(b) that the solder portion 7a is observed as images a1 and a2.

Symbol M1b denotes image data which is generated by binarizing the image data M1, and which indicates the position and extent of the solder portion 7a. Besides, symbol M2a denotes multivalued image data which is generated by multiplying the image data M1b and the image data M2, that is, by masking the image data M2 with the image data M1b. Further, image data M3 is generated by binarizing the image data M2a.

The image a1 is a gray one in the case of projecting the light on the good solder portion 7a at the wide angle $\alpha$ from the first light source 2. The steep inclined plane sb and the gentle inclined plane sc are observed dark because the light projected thereon is entirely reflected sidewards without entering the camera 1. In addition, since the electrode 6 is made of lustrous metal, the light falling on the flat top surface 6a thereof is reflected upwards, and it is observed bright.

The image a2 is a gray one in the case of projecting the light on the solder portion 7a at the narrow angle $\beta$ from the second light source 3. In this case, the light falling on the gentle inclined plane sc is reflected toward the camera 1, so that only the gentle inclined plane sc is observed bright in the shape of a ring. This image a2 is worthy of note for the following reason: It indicates that, in the case of the good solder portion, the bright ring is observed at the peripheral edge thereof, and it expresses the feature of the shape of the good solder portion clearly.

The image data M1b (image a3) generated by binarizing the image data M1, indicates the position and extent of the solder portion 7a. In the image data M2a (image a4) generated by masking the image data M2 with the image data M1b, only the steep inclined plane sb appears dark. By the way, the diameter D1 of the image a2 is somewhat smaller than that D2 of the image a3. Also, in the image data M3 (image a5) generated by binarizing the image data M2a, the steep inclined plane sb forming the shape featuring part of the solder portion 7a is favorably exhibited dark. The relations of the data items M1 thru M3 will be put in order hereunder:

(1) Binarization of M1→M1b (data of the position and extent of the solder portion)
(2) M1b×M2→M2a (data of the steep inclined plane of the solder portion)
(3) Binarization of M2a→M3 (data of the steep inclined plane forming the shape featuring part of the solder portion)

The image processing and computations as mentioned above are executed by the image processor 13. The image data M3 thus generated is stored in the third image memory 14. The image data M3 contains the feature of the shape of the solder portion 7a favorably, and it is analyzed by the CPU 15, thereby to judge whether the solder shape is good or bad. Symbol Pa in the lowermost column indicates one example of a criterion for the judgement, according to which the solder shape shall be judged good if a black ring is observed.

In the cases of the solder portion 7b of overmuch solder and the solder portion 7c of deficient solder, image data items (images) respectively shown at symbols b1-b5 and c1-c5 are similarly acquired. The reasons why such image data items are acquired, are readily understood by reference to FIGS. 2(a) thru 3(b) and the case of the solder portion 7a and shall be omitted from description. Anyway, in the case of the overmuch solder, the quality of the solder shape is judged from the image data b5. Herein, if a double black ring exists, the solder shape shall be judged to involve the overmuch solder (criterion Pb). Likewise, if a small black ring is exhibited, the solder shape shall be judged to involve the deficient solder (criterion Pc).

The prior-art method judges the quality of the solder shape from only the image data M1 picked up by the camera. In other words, it judges the quality of the solder shape on the basis of only the black information in reliance on the fact that the inclined planes are observed dark by the camera. Accordingly, the amount of information on which the judgement is founded is scanty, resulting in the problem that the method is liable to misjudge. To the contrary, the present invention is so constructed that the image data M2 containing the whit information is obtained besides the image data M1, that both the data items M1 and M2 are combined and processed, and that the quality of the solder shape is judged on the basis of the image data M3 generated by the processing. Therefore, the amount of information on which the judgement is founded is ample, and the quality can be accurately judged to that degree. Moreover, the present invention does not exclude changing-over the projection angles of light at three or more stages and thus obtaining three or more image data items. If necessary, image data may well be obtained by projecting light at an angle intermediate between the angles $\alpha$ and $\beta$.

EXAMPLE 2

Figure 5:
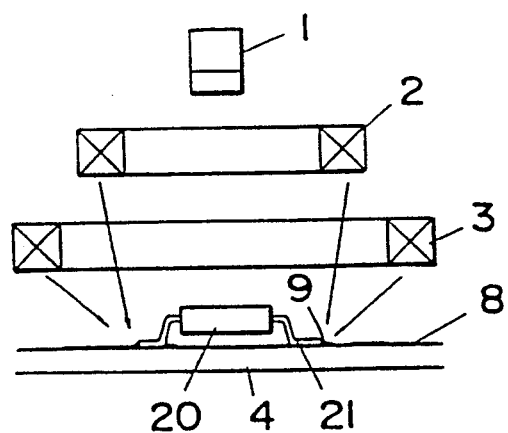
FIG. 5 is a side view of an electrical component in another example.

FIG. 5 shows a state in which an electrical component 20 having a lead 21, such as QFP or SOP, is bonded to a substrate 4 by a solder portion 9. In addition, FIG. 6 shows image data items acquired from such solder portions. The solder portion 9a which is good, the solder portion 9b which is no-good due to overmuch solder, the solder portion 9c which is no-good due to deficient solder, and the solder portion 9d which is no-good due to the floatation of the lead 21, afford the image data items A1-A5, B1-B5, C1-C5 and D1-D5, respectively. The reasons why these image data items are acquired, are readily understood by reference to FIGS. 2(a) thru 3(b) and the case of the first example and shall be omitted from description. In FIG. 6, symbols PA-PD exemplify criteria for judging whether the shape of the solder portion is good or bad.

As described above, the present invention consists in that light is projected toward a solder portion in directions of at least two angles, thereby to obtain a plurality of image data items, that the image data items are combined and processed, thereby to generate image data manifesting the feature of the solder shape favorably, and that whether the solder shape is good or bad is judged on the basis of the generated image data. Therefore, the invention can accurately judge the quality of the solder shape.

FIG. 7 shows another embodiment of this invention which is similar to the embodiment of FIGS. 1-4 except for design changes described hereinafter. With reference to FIG. 7, a first image memory 11 stored multivalue image data (multivalued image date) M1 which is obtained in the case where a solder portion 7 is exposed to a light beam from a first light source 2 and the light beam forms a wide angle $\alpha$ with respect to a plane of a circuit board or a substrate 4 (see FIG. 1). The multi-value image data M1 represents the brightness of the solder portion 7. In addition, the multi-value image data M1 contains information representing the extent or range of the solder portion 7 and the position of the solder portion 7. On the other hand, a second image memory 12 stored multi-value image data (multivalued image data) M2 which is obtained in the case where the solder portion 7 is exposed to a light beam from a second light source 3 and the light beam forms a narrow angle $\beta$ with respect to the plane of the circuit board or the substrate 4 (see FIG. 1). The multi-value image data M2 represents the brightness of the solder portion 7. In addition, the multi-value image data M2 contains information representing features of a shape of the solder portion 7. An image processor 13 includes a binarizing device 13A which receives the multi-value image data M1 from the first image memory 12, and which binarizes the multi-value image data M1 into two-value image data (binary image data) M1b. The two-value image data M1b represents the extent or range of the solder portion 7, and will be used as mask data. Specifically, the two-value mask data M1b corresponding to the inside of the range of the solder portion 7 assumes a logic value of "1", while the mask data M1b corresponding to the outside of the range of the solder portion 7 assumes a logic value of "0". The image processor 13 includes a multiplier 13B which receives the multi-value mask data M1b from the binarizing device 13A. The multiplier 13B subjects the multi-value image data M2 to a masking process using the mask data M1b. Specifically, the multiplier 13B multiplies the multi-value image data M2 and the two-value mask data M1b, nullifying the multi-value image data M2 corresponding to the outside of the range of the solder portion 7 while selecting and enabling only the multi-value image data M2 corresponding to the inside of the range of the solder portion 7. In this way, by the masking process, the multi-value image data M2 corresponding to the outside of the range of the solder portion 7 is rejected but the multi-value image data M2 corresponding to the inside of the range of the solder portion 7 is accepted. As explained later, a decision regarding the quality of a shape of the solder portion 7 will be made on the basis of only the accepted multi-value image data M2. The multiplier 13B generates and outputs multi-value image data (multivalued image data) M2a equal to a result of the multiplication between the multi-value image data M2 and the two-value mask data M1b. The multi-value image data M2a is equal to the multi-value image data M2 corresponding to the inside of the range of the solder portion 7, and represents the extent of the solder portion 7 and also the features of the shape of the solder portion 7. The image processor 13 includes a binarizing device 13C which receives the multi-value image data M2a from the multiplier 13B, and which binarizes the multi-value image data M2a into two-value image data (binary image data) M3. The two-value image data M3 is stored into a third image memory 14. A CPU 15 connected to the third image memory 14 decides whether or not the shape of the solder portion 7 is good on the basis of the image data M3 stored in the third memory 14.

We claim:

1. An apparatus for detecting a shape of a solder portion used for bonding an electrode of an electrical component to a circuit board, comprising:

a camera for observing the solder portion from above;

first light source means for projecting light toward the solder portion in a first angular direction;

a first image memory connected to said camera for storing therein first image data picked up by said camera when the first light source means projects light toward the solder portion at the first angular direction;

second light source means for projecting light toward the solder portion in a second angular direction different from the first angular direction;

a second image memory connected to said camera for storing therein second image data picked up by said camera when the second light source means projects light toward the solder portion at the second angular direction;

mask-data generating means connected to the first image memory for generating mask data from the first image data, the mask data representing a range of the solder portion;

masking means, connected to the second image memory and the mask data generating means, for accepting the second image data corresponding to an inside of the range of the solder portion and rejecting the second image data corresponding to an outside of the range of the solder portion to subject the second image data to a masking process in response to the mask data to convert the second image data into third image data; and a CPU connected to the masking means for judging a quality of the shape of the solder portion from the third image data.

2. An apparatus for detecting a shape of a solder portion used for bonding an electrode of an electrical component to a circuit board, comprising:

a camera for observing the solder portion from above;

first light source means for projecting light toward the solder portion in a first angular direction;

a first image memory connected to said camera for storing therein first multi-value image data picked up by said camera when the first light source means projects light toward the solder portion at the first angular direction;

second light source means for projecting light toward the solder portion in a second angular direction different from the first angular direction;

a second image memory connected to said camera for storing therein second multi-value image data picked up by said camera when the second light source means projects light toward the solder portion at the second angular direction;

first binarizing means connected to the first image memory for binarizing the first multi-value image data into two-value mask data representing a range of the solder portion;

multiplying means connected to the second image memory and the first binarizing means for multiplying the second multi-value image data and the two-value mask data to mask data to subject the second multi-value image data to a masking process in response to the two-value mask data to convert the second multi-value image data into third multi-value image data;

second binarizing means connected to the multiplying means for binarizing the third multi-value image data into two-value image data;

a third image memory connected to the second binarizing means for storing therein the two-value image data; and a CPU connected to the third image memory for judging a quality of the shape of the solder portion from the two-value image data stored in the third image memory.

3. A method of detecting a shape of a solder portion used for bonding an electrode of an electrical component to a circuit board, comprising the steps of:

observing the solder portion from above by using a camera;

projecting light toward the solder portion in a first angular direction;

generating first image data by said camera when light is projected toward the solder portion at the first angular direction;

projecting light toward the solder portion in a second angular direction different from the first angular direction;

generating second image data by said camera when light is projected toward the solder portion at the second angular direction;

generating mask data from the first image data, the mask data representing a range of the solder portion;

accepting the second image data corresponding to an inside of the range of the solder portion and rejecting the second image data corresponding to an outside of the range of the solder portion to subject the second image data to a masking process in response to the mask data to convert the second image data into third image data; and judging a quality of the shape of the solder portion from the third image data.

4. A method of detecting a shape of a solder portion used for bonding an electrode of an electrical component to a circuit board, comprising the steps of:

observing the solder portion from above by using a camera;

projecting light toward the solder portion in a first angular direction;

generating first multi-value image data by said camera when light is projected toward the solder portion at the first angular direction;

projecting light toward the solder portion in a second angular direction different from the first angular direction;

generating second multi-value image data by said camera when light is projected toward the solder portion at the second angular direction;

binarizing the first multi-value image data into two-value mask data representing a range of the solder portion;

multiplying the second multi-value image data and the two-value mask data to subject the second multi-value image data to a masking process in response to the two-value mask data to convert the second multi-value image data into third multi-value image data;

binarizing the third multi-value image data into two-value image data; and judging a quality of the shape of the solder portion from the two-value image data.

* * * * *